United States Patent [19]

Kubicek

[11] 3,994,980
[45] Nov. 30, 1976

[54] COBALT MOLYBDATE AS CATALYST FOR PREPARATION OF MERCAPTANS FROM CARBONYL COMPOUNDS HYDROGEN SULFIDE AND HYDROGEN

[75] Inventor: Donald H. Kubicek, Bartlesville, Okla.

[73] Assignee: Phillips Petroleum Company, Bartlesville, Okla.

[22] Filed: Oct. 15, 1975

[21] Appl. No.: 622,590

[52] U.S. Cl. .......................... 260/609 R; 260/609 D
[51] Int. Cl.² ...................................... C07C 148/00
[58] Field of Search ................................ 260/609 R

[56] References Cited
UNITED STATES PATENTS

| | | | |
|---|---|---|---|
| 2,402,613 | 6/1946 | Farlow et al. | 260/609 R |
| 2,402,614 | 6/1946 | Farlow et al. | 260/609 R |
| 2,402,694 | 6/1946 | Tanner | 260/609 R |
| 2,406,410 | 8/1946 | Signaigo | 260/609 R |
| 2,514,300 | 7/1950 | Laughlin | 260/609 R |
| 2,796,438 | 6/1957 | Martin et al. | 260/609 R |
| 2,820,062 | 1/1958 | Folkins et al. | 260/609 R |
| 3,198,839 | 8/1965 | Phillippe | 260/609 R |

FOREIGN PATENTS OR APPLICATIONS

| | | | |
|---|---|---|---|
| 227,934 | 10/1966 | U.S.S.R. | 260/609 R |

Primary Examiner—Elbert L. Roberts
Assistant Examiner—D. R. Phillips

[57] ABSTRACT

Mercaptans are prepared by reacting an organic carbonyl compound with sulfur or hydrogen sulfide in the presence of a catalyst consisting essentially of cobalt, molybdenum and an inorganic oxide support material.

17 Claims, No Drawings

COBALT MOLYBDATE AS CATALYST FOR PREPARATION OF MERCAPTANS FROM CARBONYL COMPOUNDS HYDROGEN SULFIDE AND HYDROGEN

This invention relates to a process for the production of mercaptans.

It is known that mercaptans can be obtained by the reaction of hydrogen sulfide or sulfur and hydrogen with an organic carbonyl compound, such as carboxylic acids, aldehydes and ketones in the presence of a catalyst.

The sulfides of molybdenum, tungsten, cobalt or copper have been employed as catalysts for this reaction; however, such catalysts have generally resulted in very low yields, on the order of 20 percent.

Greater yields, on the order of 40 percent, can be obtained at elevated temperatures and pressures, substantially greater than 300° C and 300 atmospheres. Such high temperatures and pressures cannot be used for many compounds without risk of decomposition.

It is therefore an object of this invention to provide a new and improved method of forming mercaptans from oxygen-containing organic compounds.

Another object is to provide a method for preparing mercaptans at a temperature low enough to minimize the risk of decomposition.

A further object is to provide a process for preparing mercaptans in which improved yields are obtained.

Other objects, aspects and advantages of this invention will be readily apparent to those skilled in the art from the reading of the following disclosure.

In accordance with the present invention there is provided a process for the preparation of a mercaptan which comprises reacting an organic compound containing a carbonyl group with a sulfur source such as elemental sulfur or hydrogen sulfide in the presence of a catalyst consisting essentially of from about 0.8 to about 8 weight percent cobalt, from about 4 to about 24 weight percent molybdenum and from about 52 to about 94 weight percent of an inorganic oxide support material, with the remainder being oxygen or sulfur in an amount sufficient to satisfy the valence requirements of cobalt and molybdenum. Optionally, the process is conducted in the presence of hydrogen.

The carbonyl compounds useful in the preparation of mercaptans according to the present invention have up to 20 carbon atoms, preferably up to 10 carbon atoms, per molecule and can be represented by the formula

wherein R is selected from the group consisting of hydrogen, alkyl, cycloalkyl, aryl and combinations thereof, such as aralkyl and alkaryl; and Y is selected from the group consisting of —R, —OR, —SR, —NR$_2$, —O$_2$CR and halogen, such as chlorine, bromine, iodine and fluorine; and wherein R and Y can be alkylene groups connected together to form a carbocyclic ring.

Examples of useful carbonyl compounds include acetone, 2-butanone, 3-hexanone, 6-eicosanone, acetophenone, cyclohexanone, formaldehyde, acetaldehyde, benzaldehyde, p-tolualdehyde, α-tolualdehyde, formic acid, acetic acid, hexanoic acid, capric acid, stearic acid, benzoic acid, cyclohexane carboxylic acid, methyl formate, ethyl acetate, methyl benzoate, acetic anhydride, propionic anhydride, benzoic anhydride, acetyl chloride, benzoyl chloride, thioacetic acid, thiostearic acid, acetamide, butyramide, benzamide and N-phenylbenzamide.

The sulfur source can be hydrogen sulfide or elemental sulfur. Hydrogen sulfide can be utilized in the absence of added hydrogen, however, more satisfactory results are achieved when hydrogen is also used.

The amount of the sulfur source used is in the range of 1 to 25 moles per mole of carbonyl compound. When hydrogen is used the amount used is in the range of 0.1 to 10 moles of hydrogen per mole of carbonyl compound. It is also within the scope of this invention to use a greater quantity of either the sulfur source, the hydrogen or both should conditions of temperature, pressure, conversion or product distribution so require. In general, however, the amounts expressed above will be used.

The process of this invention can, if desired, be conducted in the presence of an inert diluent in the reaction system. Suitable diluents include hydrocarbons such as pentane, octane, and the like, and water.

The catalyst consists essentially of the oxides or sulfides of cobalt and molybdenum, all supported on an inorganic oxide support such as alumina, alumino-silicates and Group II aluminate spinels, such as zinc aluminate spinel. The supported catalyst contains from about 0.8 to about 8 weight percent cobalt, from about 4 to about 24 weight percent molybdenum and from about 52 to about 94 weight percent support with the remainder being oxygen or sulfur in an amount sufficient to satisfy the valence requirements of cobalt and molybdenum.

In a presently preferred embodiment the catalyst contains from about 1.6 to about 4 weight percent cobalt and from about 8 to about 16 weight percent molybdenum, and the support is alumina.

The catalyst employed in this invention can be prepared by any suitable method such as by coprecipitation, impregnation or by dry mixing cobalt oxide, molybdenum oxide and the support material in the desired quantities. Other methods of preparation known in the art can also be used.

If the metal oxides are used to prepare the catalyst, it may be desirable to sulfide the catalyst before use. Sulfiding can be carried out by heating the catalyst in the presence of hydrogen sulfide, or by other methods known in the art. It is, however, not necessary to employ a prior sulfiding step, because the catalyst is believed to become sulfided under reaction conditions.

Should the catalyst become inactive after use, it can be regenerated by calcination in air.

The process of this invention is carried out at a temperature in the range of 300°–700° F (150°–370° C), preferably 400° to 550° F (200°–290° C) and a pressure in the range from 0 to 5000 psig (100–34,500 kPa), preferably 150–1000 psig (1140–6,980 kPa).

The process of this invention can be conducted batchwise or in continuous fashion. The process is particularly well suited for continuous operation.

In a batch process the amount of catalyst employed ranges from about 5 to about 25 weight percent of the carbonyl compound. Contact time in a batch reactor is highly dependent upon the temperature, pressure, reactant reactivity, desired conversion, desired product distribution and the like. Contact times ranging from 15 minutes to 15 hours are generally adequate to produce the desired results.

In a continuous process the contact time and amount of catalyst, expressed in terms of liquid hourly space velocity (LHSV), i.e., liquid volume of reactant per volume of catalyst per hour, is dependent upon the factors of temperature, pressure, etc., expressed above. An LHSV ranging from 0.1 to 10, preferably from 0.5 to 5 is generally adequate to produce the desired results. It is presently preferred that the process of this invention be conducted in a continuous fashion.

It is also within the scope of this invention to have present in the reactor system other materials, such as alcohols, which are capable of being converted to mercaptans under conditions of the present invention. Thus, a mixed feed containing a carbonyl compound, as defined above, and an alcohol, in any proportion, can be readily converted to the corresponding mercaptans in accordance with the process of the present invention. For example, a mixture of cyclohexanone and cyclohexanol can be readily converted to cyclohexyl mercaptan.

The mercaptan product of the process of this invention can be recovered in any conventional manner, such as by distillation. When separation by distillation is not feasible, such as when the product mercaptan, the unconverted cabonyl compound and, if present, the alcohol, have closely related boiling points, separtion can be effected by extracting the product mixture with water. For example, cyclohexyl mercaptan can be readily separated from a mixture of cyclohexanone, cyclohexanol and cyclohexyl mercaptan by washing the mixture with water.

The following example illustrates the invention:

EXAMPLE I

A conventional stainless steel tubular reactor ½-inch diameter and 18 inches long fitted with a ¼-inch diameter internal thermocouple well extending the length of the reactor was utilized in the following runs. The catalyst (50 g, about 75 cc) employed consisted essentially of 3–4 weight percent cobalt oxide and 15–16 percent molybdenum oxide supported on alumina. It was sulfided by contact with flowing hydrogen sulfide for 4 hours at 600° F before contact with the feedstock. The reactor was electrically heated. A gas chromatograph was employed for product analysis.

Runs 1 to 20 were conducted in the above described reactor employing feed and conditions tabulated in Table I:

Table I

| Run No. | Carbonyl Comp. | $H_2S/CC^a$ | Feed Ml/Min | $H_2$ Mole/Hr | Temp., °F | Press. Psig | Product Mercaptan | Area %$^b$ Reaction Mixture CC | RSH | $R_2S$ | Other | % Conv.$^i$ | % Select.$^i$ to RSH |
|---|---|---|---|---|---|---|---|---|---|---|---|---|---|
| 1 | Acetic Acid | 6 | 2 | 0.8 | 500 | 450 | Ethyl mercaptan | 0.1 | 86 | 11.3 | 1.8 | 100 | 87 |
| 2 | Ethyl Acetate | 8.8 | 2 | 0.8 | 400 | 450 | Ethyl mercaptan | 56.5 | 24.3 | 1.4 | 15.3 | 42 | 59 |
| 3 | Ethyl Acetate | 8.8 | 2 | 0.8 | 450 | 450 | Ethyl mercaptan | 46.7 | 40.4 | 2.2 | 8.3 | 52 | 79 |
| 4 | Ethyl Acetate | 8.8 | 2 | 0.8 | 500 | 450 | Ethyl mercaptan | 9.3 | 74.9 | 10.3 | 3.6 | 91 | 84.5 |
| 5 | Methyl Benzoate | 10 | 2 | 0.8 | 450 | 450 | Benzyl mercaptan | 0.2 | 14.1 | | 85.2$^c$ | 100 | 14 |
| 6 | Formaldehyde$^d$ | 3 | 0.5 | 0.8 | 450 | 180 | Methyl mercaptan | 0 | 27.8 | 0.7 | 71.6$^e$ | 100 | 83 |
| 7 | n-Butyraldehyde$^f$ | 23 | 2 | 0.8 | 400–500 | 450 | n-Butyl mercaptan | | g | | | | |
| 8 | Benzaldehyde | | 0.5 | 0.8 | 350–500 | 450 | Benzyl mercaptan | | h | | | | |
| 9 | Acetone | 3 | 2 | 0.8 | 450 | 450 | Isopropyl mercaptan n-Propyl mercaptan | 3.4 | 86.1 1.3 | | 6.2 | 96.5 | 92 1.4 |
| 10 | Acetone | 3 | 2 | 0.8 | 500 | 450 | Isopropyl mercaptan n-Propyl mercaptan | 0.7 | 84.1 8.8 | | 3.6 | 99 | 87 9.1 |
| 11 | Acetone | 6 | 2 | 0 | 500–600 | 450 | Isopropyl mercaptan n-Propyl mercaptan 1,2-Propanedithiol | 0 | 45 22 11 | | 22 | 100 | 45 22 11 |
| 12 | Acetone/Isopropanol | j | 2 | 0.8 | 450 | 450 | Isopropyl mercaptan n-Propyl mercaptan | 29$^k$ | 65.5 2.2 | | 0.6 | 70 | 96 3.2 |
| 13 | Acetone/Isopropanol | j | 2 | 0.8 | 500 | 450 | Isopropyl mercaptan n-Propyl mercaptan | 5.4$^k$ | 79 10.7 | | 2.1 | 94 | 86 12 |
| 14 | Acetone/Isopropanol | j | 2 | 0.8 | 550 | 450 | Isopropyl mercaptan n-Propyl mercaptan | 0.6$^k$ | 68.8 23.6 | | 4.2 | 99 | 71 24 |
| 15 | Cyclohexanone | 3 | 0.5$^l$ | 0.8 | 400 | 180 | Cyclohexyl mercaptan | 1.6 | 64.4 | 14.8 | 19.1$^m$ | 98 | 64.8 |
| 16 | Cyclohexanone | 3 | 0.5$^l$ | 0.8 | 450 | 180 | Cyclohexyl mercaptan | 0.3 | 83.2 | 2.2 | 14.2$^m$ | 99.7 | 83.4 |
| 17 | Cyclohexanone | 3 | 0.5$^l$ | 0.8 | 500 | 180 | Cyclohexyl mercaptan | — | 63.8 | 4.4 | 31.8$^m$ | 100 | 59.8 |
| 18 | Cyclohexanone/cyclohexanol | n | 0.17$^l$ | 0.8 | 400 | 450 | Cyclohexyl mercaptan | 7.4 | 70.7 | 2.8 | 19.1$^m$ | 92.1 | 64.7 |
| 19 | Cyclohexanone/cyclohexanol | n | 0.17$^l$ | 0.8 | 450 | 450 | Cyclohexyl mercaptan | 0.3 | 74.7 | 10.2 | 14.9$^m$ | 99.7 | 69.3 |
| 20 | Cyclohexanone/cyclohexanol | n | 0.17$^l$ | 0.8 | 500 | 450 | Cyclohexyl mercaptan | 0.1 | 66.1 | 4.3 | 29.6$^m$ | 99.9 | 58.9 |

$^a$Hydrogen sulfide/carbonyl compound molar ratio in feed.
$^b$Area percent by glc excluding residual hydrogen sulfide, except as noted.
$^c$Major product is toluene.
$^d$37 percent aqueous formaldehyde containing 10–15 percent methanol.
$^e$Contains major amount of hydrogen sulfide.
$^f$n-Butyraldehyde was 50 percent pure.
$^g$Product mixture was complex, but n-butyl mercaptan was the major product.
$^h$Glc showed only a few percent yield of benzyl mercaptan. Major products were bibenzyl and toluene.
$^i$Conversion and selectivity were based on glc area percents.
$^j$$H_2S$/Acetone = 6; $H_2S$/isopropanol = 6.
$^k$Includes both acetone and isopropanol. Not separated by glc.
$^l$Mole/hr instead of ml/min.
$^m$Contains benzene, cyclohexene, cyclohexane and unidentified components.
$^n$$H_2S$/cyclohexanone = 12; $H_2S$/cyclohexanol = 12.

The above data illustrate that a wide variety of carbonyl compounds can be converted to mercaptans according to the process of this invention. Runs 12 to 14 and 18 to 20 further illustrate that mixtures of ketones and alcohols were readily converted to mercaptans.

EXAMPLE II

For comparison, a catalyst consisting essentially of 10 weight percent cobalt oxide on alumina was employed in the following runs. 66 Grams of the catalyst (about 59 cc) were placed in the reactor employed in Example I. The catalyst was sulfided by contact with flowing hydrogen sulfide for 2 hours at 600° F before contact with the feedstock.

Runs 21 to 27 were contacted in the previously described reactor employing the feed and conditions tabulated in Table II.

Table II

Reactions Over Cobalt-Containing Catalyst

| Run No. | Carbonyl Comp. | $H_2S/CC^a$ | Feed Ml/Min | $H_2$ Mole/Hr | Temp., °F | Press. Psig | Product Mercaptan | Area %$^b$ Reaction Mixture, CC | RSH | $R_2S$ | Other | % Conv.$^c$ | % Select.$^c$ to RSH |
|---|---|---|---|---|---|---|---|---|---|---|---|---|---|
| 21 | Acetic acid | 6 | 2.0 | 0.8 | 400 | 450 | Ethyl Mercaptan | 99.2 | nd | — | 0.8 | 0.8 | 0 |
| 22 | Acetic acid | 6 | 2.0 | 0.8 | 450 | 450 | Ethyl Mercaptan | 99.0 | 0.1 | — | 0.9 | 1.0 | 10 |
| 23 | Acetic acid | 6 | 2.0 | 0.8 | 500 | 450 | Ethyl Mercaptan | 97.4 | 1.2 | — | 1.4 | 2.2 | 54.5 |
| 24 | Cyclohexanone | 3 | 0.5$^d$ | 0.8 | 400 | 180 | Cyclohexyl Mercaptan | 7.9 | 53.8 | 0.9 | 37.4 | 90.9 | 58.1 |
| 25 | Cyclohexanone | 3 | 0.5$^d$ | 0.8 | 450 | 180 | Cyclohexyl Mercaptan | 6.9 | 75.9 | 1.5 | 15.7 | 92.2 | 79.0 |
| 26 | Cyclohexanone | 3 | 0.5$^d$ | 0.8 | 500 | 180 | Cyclohexyl Mercaptan | 0.3 | 71.5 | 2.3 | 25.9 | 99.7 | 66.0 |

$^a$Hydrogen sulfide/carbonyl compound molar ratio in feed.
$^b$Area percent by glc excluding residual hydrogen sulfide, except as noted.
$^c$Conversion and selectivity were based on glc area percents.
$^d$Mole/hr rather than ml/min.

It can be seen from the above data that a supported cobalt oxide catalyst is ineffective to convert acetic acid to ethyl mercaptan. In contrast, as shown in run 1, Table I, the process of the present invention can be used to convert acetic acid to ethyl mercaptan in high yield.

The above data also illustrate that the conversion of cyclohexanone to cyclohexyl mercaptan can be carried out according to the present invention at lower temperatures. A comparison of run 24, above, with run 15, Table I, shows that at the same operating conditions, i.e., same ratio of hydrogen sulfide to carbonyl compound, same feed rate, hydrogen rate, temperature and pressure, the process of the present invention provides at least 20 percent improvement in yield of cyclohexyl mercaptan. Comparison of run 25, above, with run 16, Table I, shows that the process of this invention provides an increased yield of cyclohexyl mercaptan of greater than 14 percent. Comparison of run 26, above, with run 17, Table I, shows that the catalyst employed in the present invention behaves differently than the catalyst employed in runs 24–26. Had the catalysts been the same, the trend seen by a comparison of runs 15 and 16 with runs 24 and 25 would also have been seen in comparing runs 17 and 26.

Reasonable variations and modifications, which will be apparent to those skilled in the art, can be made in this invention without departing from the spirit and scope thereof.

What is claimed is:

1. A process for the preparation of a mercaptan which comprises contacting a mixture of an organic compound containing a carbonyl group, a sulfur source selected from the group consisting of hydrogen sulfide and sulfur, and hydrogen with a catalyst consisting essentially of from about 1.6 to about 4 weight percent cobalt, from about 8 to about 16 weight percent molybdenum, and from about 70 to about 88 weight percent of an inorganic oxide support material with the remainder being oxygen or sulfur in an amount sufficient to satisfy the valence requirements of said cobalt and said molybdenum, said contacting being carried out at a temperature in the approximate range of 400° to 550° F and a pressure in the approximate range of 150 to 1000 psig.

2. The process of claim 1 wherein said catalyst consists essentially of 3 to 4 weight percent cobalt oxide and 15 to 16 weight percent molybdenum oxide on an alumina support, said catalyst being sulfided by contact with flowing hydrogen sulfide at an elevated temperature.

3. The process of claim 1 wherein said organic compound has up to 20 carbon atoms per molecule and is represented by the formula

wherein R is selected from the group consisting of hydrogen, alkyl, cycloalkyl, aryl, and combinations thereof; and Y is selected from the group consisting of —R, —OR, —SR, —NR$_2$, —O$_2$CR and halogen; and wherein R and Y can be alkylene groups connected together to form a carbocyclic ring.

4. The process of claim 3 wherein said organic compound has up to 10 carbon atoms per molecule.

5. The process of claim 1 wherein said sulfur source is employed in an amount ranging from 1 to 25 moles per mole of said organic compound.

6. The process of claim 5 wherein said hydrogen is employed in an amount ranging from 0.1 to 10 moles per mole of said organic compound.

7. The process of claim 1 wherein said sulfur source and said organic compound are contacted with said catalyst at a liquid hourly space velocity for said organic compound in the approximate range of 0.1 to 10.

8. The process of claim 1 wherein said sulfur source is hydrogen sulfide and said organic compound is acetic acid.

9. The process of claim 1 wherein said sulfur source is hydrogen sulfide and said organic compound is ethyl acetate.

10. The process of claim 1 wherein said sulfur source is hydrogen sulfide and said organic compound is methyl benzoate.

11. The process of claim 1 wherein said sulfur source is hydrogen sulfide and said organic compound is formaldehyde.

12. The process of claim 1 wherein said sulfur source is hydrogen sulfide and said organic compound is benzaldehyde.

13. The process of claim 1 wherein said sulfur source is hydrogen sulfide and said organic compound is n-butyraldehyde.

14. The process of claim 1 wherein said sulfur source is hydrogen sulfide and said organic compound is acetone.

15. The process of claim 1 wherein said sulfur source is hydrogen sulfide and said organic compound is cyclohexanone.

16. The process of claim 1 wherein said sulfur source is hydrogen sulfide and said organic compound is a mixture of acetone and isopropanol.

17. The process of claim 1 wherein said sulfur source is hydrogen sulfide and said organic compound is a mixture of cyclohexanone and cyclohexanol.

* * * * *